United States Patent [19]
Lock et al.

[11] Patent Number: 5,383,926
[45] Date of Patent: Jan. 24, 1995

[54] RE-EXPANDABLE ENDOPROSTHESIS

[75] Inventors: James E. Lock, Newton; Valerie Mandell, Brookline; Stanton Perry, Swampscott, all of Mass.

[73] Assignee: Children's Medical Center Corporation, Boston, Mass.

[21] Appl. No.: 980,300

[22] Filed: Nov. 23, 1992

[51] Int. Cl.⁶ .................................................. A61F 2/04
[52] U.S. Cl. ............................................ 623/1; 623/12; 606/198
[58] Field of Search ............... 623/1, 11, 12; 606/198, 606/195, 194, 192, 191, 108

[56] References Cited

U.S. PATENT DOCUMENTS

| | | | |
|---|---|---|---|
| 4,830,003 | 5/1989 | Wolff et al. | 623/1 |
| 5,007,926 | 4/1991 | Derbyshire | 623/1 |
| 5,135,536 | 8/1992 | Hillstead | 606/195 |
| 5,192,307 | 3/1993 | Wall | 623/12 |

*Primary Examiner*—Stephen C. Pellegrino
*Assistant Examiner*—M. Peffley
*Attorney, Agent, or Firm*—Reising, Ethington, Barnard, Perry & Milton

[57] ABSTRACT

A radially expandable endoprosthesis device (10) comprises an elongated sleeve member (12) in which the radially outward expansion of the sleeve member (12) is initially limited by connecting strips (22) which are operatively connected to the sleeve member (12). The connecting strips (22) are selectively removable to allow further radial outward expansion. Further, the sleeve can be C-shaped in cross sections when expanded, allowing space for growth of a vessel contained therein.

14 Claims, 1 Drawing Sheet

RE-EXPANDABLE ENDOPROSTHESIS

TECHNICAL FIELD

The present invention relates to an endoprosthesis device for implantation within a body vessel, typically a blood vessel and which allows for additional expansions of the endoprosthesis to accommodate, for example, continued outward circumferential growth of the vessel.

BACKGROUND OF THE INVENTION

Endoprosthetic devices, commonly referred to as stents, are generally implanted to reinforce vessel walls. In one type, the stent is implanted via a catheter by mounting the stent in a collapsed form on the catheter. After positioning the stent in a body vessel, the stent is expanded to a larger diameter either by self-expansion or by the use of a balloon catheter or the like and the catheter removed. These stents have generally included cylindrical springs of stainless steel, sleeves of expandable heat sensitive materials, and expandable sleeves formed of linked metal alloy wires arranged in a zig-zag configuration and expandable metal mesh sleeves as shown in United States Patents: U.S. Pat. No. 4,733,665 to Palmaz issued Mar. 29, 1988; U.S. Pat. No. 4,776,337 to Palmaz issued Oct. 11, 1988; U.S. Pat. No. 4,856,516 to Hillstead issued Aug. 15, 1989; U.S. Pat. No. 4,877,030 to Beck et al. issued Oct. 31, 1989; U.S. Pat. No. 5,007,926 to Derbyshire issued Apr. 16, 1991; U.S. Pat. No. 5,019,090 to Pinchuk issued May 28, 1991; U.S. Pat. No. 5,041,126 to Gianturco issued Aug. 20, 1991; U.S. Pat. No. 5,102,417 to Palmaz issued Apr. 7, 1992; U.S. Pat. No. 5,104,404 to Wolff issued Apr. 14, 1992; U.S. Pat. No. 5,122,154 to Rhodes issued Jun. 16, 1992; U.S. Pat. No. 5,133,732 to Wiktor issued Jul. 28, 1992; U.S. Pat. No. 5,135,536 to Hillstead issued Aug. 4, 1992.

Over time, prior art stents may require an additional or secondary dilation to accommodate or effect further changes in the vessel. The elastic recoil associated with stenotic lesions may require a second dilation to prevent restenosis. The above configurations allow for secondary dilation, but only to a maximum based on the stent design.

Further, a major problem with the use of stents in pediatric patients is that the vessel stops growing where the stent is implanted, particularly where a metal mesh sleeve stent is employed. The adherence of the endothelial cellular layer of the vessel to the stent surface tends to prevent further outward circumferential growth of the vessel. Further growth is required in body vessels of pediatric patients. The use of wire stents that have a low surface area and which may allow endothelial growth are not optimal because of the high local stress on the vessel wall caused by the wires.

Of course, one option is to replace the stent on a regular basis, but this would involve repeated surgeries which both increase costs and risks for the patient. The present stents would only bemused in a small child in an emergency due to the limitation of these stents.

The prior art discloses stents which are circumferentially expandable such as the Beck et al. '030 patent. The Beck et al. '030 patent discloses an endoprosthesis for vessels in which a "rolled-up" uninflated stent is placed over an uninflated balloon catheter and inserted into the target vessel. Once in position, the catheter is inflated, thereby "unrolling" and dilating the prosthesis to form a tube-like structure. The catheter is then removed. A second possible dilation of the endoprosthesis is not provided. Further, no provision is made for use in pediatric patients requiring circumferential growth of the vessel.

The Palmaz '665 patent also describes a variable expandable intraluminal vascular stent in which the stent is a wire mesh tube. However no provision is made for circumferential growth of the body vessel or any later secondary dilation of the endoprosthesis because it is limited by a maximum diameter based on the stent design.

SUMMARY OF THE INVENTION AND ADVANTAGES

According to the present invention, a radially expandable endoprosthesis device comprises an elongated sleeve member. The sleeve member has a longitudinal axis extending through its length. The sleeve member is expandable radially outwardly relative to the longitudinal axis. The radially outward expansion of the sleeve member is initially limited by expansion limiting means which are operatively connected to the sleeve member. The expansion limiting means are selectively removable to allow further radial outward expansion.

This invention has the advantage that it allows for the endoprosthesis to be re-expanded to a larger circumference as needed to accommodate vessel change. The endoprosthesis is implanted and expands to its initial circumference. At some point in the future, perhaps as required by restenosis or growth, a secondary expansion is possible.

A further feature of the present invention allows for circumferential growth of the vessel by the presence in the sleeve member of a lateral slot, giving a C-shape to the sleeve. Therefore a section of the vessel wall located in the opening of the "C" is not adhering to the endoprosthesis thereby allowing circumferential growth in that region.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE PREFERRED EMBODIMENT

Figure 3:
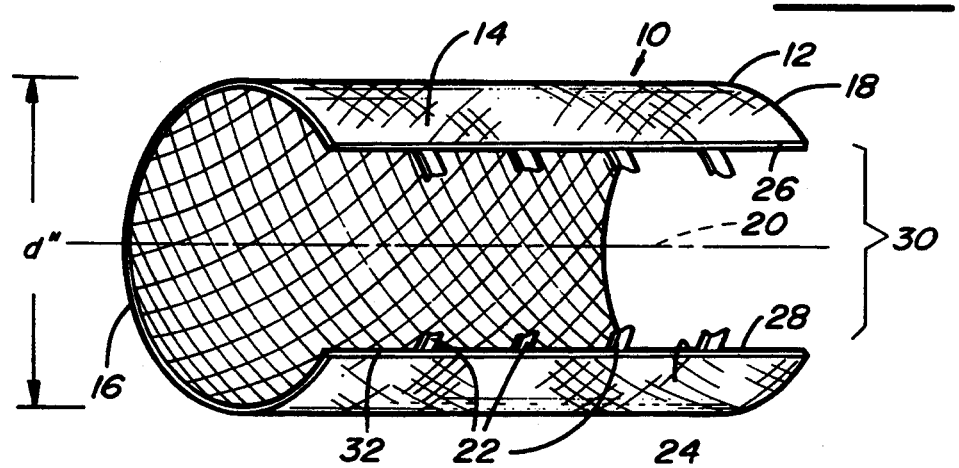
FIG. 3 is a side view of a preferred embodiment of a radially expandable endoprosthesis device according to the instant invention in a secondarily expanded configuration.

Referring to the figures, an endoprosthesis device constructed in accordance with the instant invention is generally shown at 10. The endoprosthesis device 10 includes an elongated sleeve member 12. The elongated sleeve member 12 has an essentially tube-like configuration including a wall 14 and extends longitudinally along its length ending at opposite ends 16,18. The sleeve member 12 has a longitudinal axis 20 extending through the length as shown in FIG. 3 and has a circumference with a diameter d.

Figure 1:
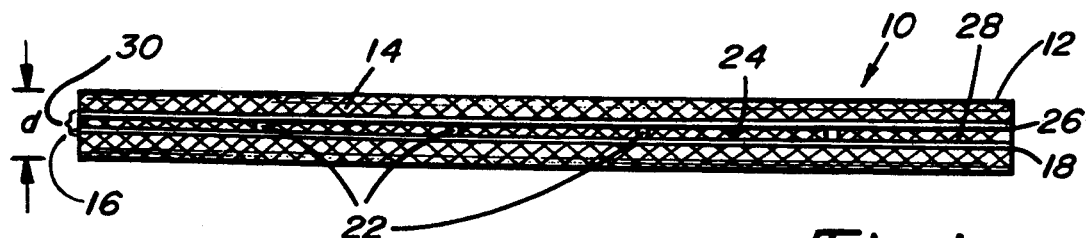
FIG. 1 is a side view of a preferred embodiment of a radially expandable endoprosthesis device according to the instant invention in an unexpanded configuration.
Figure 2:
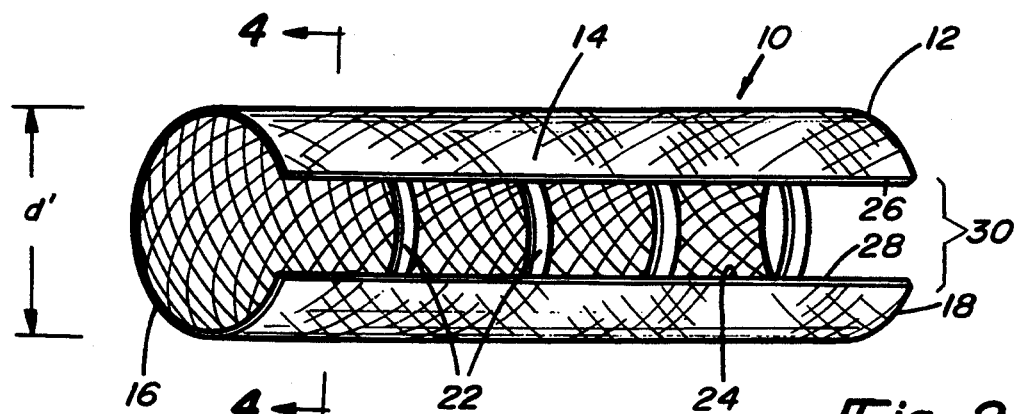
FIG. 2 is a side view of a preferred embodiment of a radially expandable endoprosthesis device according to the instant invention in an initially expanded configuration.
Figure 4:
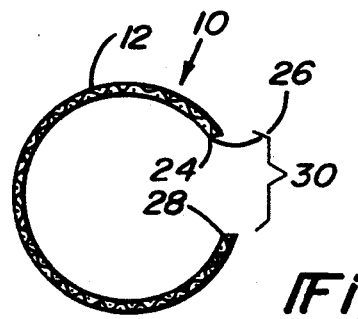
FIG. 4 is a cross sectional view of a preferred embodiment along line 4—4 of FIG. 2.

The sleeve member 12 is outwardly radially expandable with reference to the longitudinal axis 20. That is, the circumference can be enlarged or expanded as best shown in FIGS. 1-3. In the unexpanded state, the circumference is at its minimum with a diameter d of 1.5 to 5 mm as shown in FIG. 1. When expanded initially, the circumference is expanded to a first circumference with a first diameter d', of 3 to 18 mm, as shown in FIG. 2. If expanded secondarily, the first circumference is expanded to a second circumference with a second diameter d". The diameter d" is without limit in the sense that the open stent provides no limit to circumferential growth of the vessel, as shown in FIGS. 3 and 4.

The sleeve member 12 is generally fabricated from various biocompatible metal alloys including from expandable heat-sensitive materials and memory alloys. The sleeve member 12 can also be configured as either variations on a helical coil, a coiled spring, a zig-zag pattern or a wire mesh tube with the preferred embodiment being similar to the wire mesh tube such as is disclosed in the Palmaz '337 patent.

The radially outward expansion of the circumference of the sleeve member 12 is limited to the first circumference initially by expansion limiting means operatively connected to the sleeve member 12. The expansion limiting means are selectively removable to allow further radial outward expansion to the second circumference.

The expansion limiting means in one embodiment is composed of a pressure sensitive material such as nonabsorbable suture. In a preferred embodiment the pressure sensitive material is one that ruptures above 4-10 atm pressure. Alternatively, the expansion limiting means is composed of a dissolvable material such as an absorbable suture made from polyglactin (Vicryl TM) or a nonabsorbent material such as polypropylene, nylon, silk, or polyester.

In one embodiment the expansion limiting means includes at least one connecting strip 22 which acts to limit radial outward expansion of the sleeve member 12. Preferably, the dimension of the strip is 0.1-2 mm, providing one to four strips per centimeter.

In an embodiment utilizing the connecting strip 22, it is circumferentially disposed about the sleeve member 12. Therefore, the sleeve member 12 can only initially expand to the limit of the connecting strip 22 that is girdling the sleeve member 12.

In the preferred embodiment, the sleeve member 12 includes at least one lateral slot 24 in the wall 14 parallel to the longitudinal axis 20 and extending between the opposite ends 16,18. The lateral slot 24 includes a pair of opposing edges 26,28 which extend parallel to the longitudinal axis 20. The opposing edges 26,28 define an open region 30 between them. The connecting strip 22 operatively connects the opposing edges 26,28 of the lateral slot 24 across the open region 30. A radiopaque material, such as platinum, may be disposed along the opposing edges 26,28 for imaging.

In a second embodiment, the expansion limiting means includes a sheet of material that is disposed across the open region 30. The sheet of material is composed of an expandable material such as Goritex ®. In the unexpanded configurations as shown in FIG. 1, the sheet of material is disposed within the sleeve member 12. In the expanded configuration, as shown in FIGS. 2 and 3, the material is stretched across the open region 30.

To fabricate the endoprosthesis device 10, the radially expandable sleeve member 12 and expansion limiting means are formed. The expansion limiting means are then operatively connected to the sleeve member 12 such that they initially limit the radial outward expansion of the sleeve member 12.

In the preferred embodiment, the sleeve member 12 is formed from a wire mesh tube and at least one lateral slot 24 is cut through the wall 14 and extending the entire length and parallel to the longitudinal axis 20. Alternatively, the slot 24 can be staggered or non-parallel to the longitudinal axis 20.

The expansion limiting means are then formed into at least one connecting strip 22 which is operatively connected to the opposing edges 26,28 of the lateral slot 24 across the open region 30. In the preferred embodiment, one to four connecting strips of 0.1-2 millimeter width are required per centimeter of length connected. The connecting strip 22 is secured to the sleeve member 12 in any conventional manner, such as by welding, soldering, gluing as known to those skilled in the art.

The endoprosthesis device 10 can be used to initially reinforce or dilate the lumen of a body vessel such as arteries, veins or ducts, followed by a secondary reinforcement or dilation to accommodate changes in the vessel. In the preferred embodiment, the endoprosthesis device 10 is mounted on a catheter in an unexpanded configuration and inserted transluminally within a body vessel in a conventional manner. The unexpanded circumference with diameter d is needed in order to permit passage through body vessels until the desired position is reached.

Fluoroscopy, and/or other conventional techniques may be utilized to ensure that the catheter and endoprosthetic device 10 are properly positioned. Proper positioning can include positioning the endoprosthesis device 10 in the body vessel to accommodate branching vessels. To accomplish this the lateral slot 24 is positioned in front of the branching vessel. Positioning of the lateral slot 24 can be assisted by a radiopaque lining 32 of the opposing edges 26,28 of the lateral slot 24.

Once the endoprosthesis device 10 is delivered to the desired location, the sleeve member 12 is expanded radially outwardly to the first diameter d'. The initial or first expansion can be accomplished by a conventional angioplasty balloon utilizing a pressure of less than about eight atmospheres (M. O'Laughlin et al., *Use of Endovascular Stents in Congenital Heart Disease*, Circulation 1991, 83:1923-1937). The initial expansion of the sleeve member 12 is limited to the first circumference by limiting means. To provide secondary expansion to the second circumference the limiting means are later removed.

The initial expansion is limited in the preferred embodiment by the connecting strip 22 operatively connecting the opposing edges 26,28 of the lateral slot 24. That is, the circumferencial expansion across the lateral slot 24 is limited by the connecting strip 22 which will not disjoin or rupture at the pressure used for initial expansion. When the expansion is stopped across the lateral slot 24, the overall expansion of the sleeve member 12 is impeded and stops since the balloon catheter is exerting force equally. In other words, the connecting strip 22 causes the sleeve member 12 to girdle the balloon catheter preventing its further expansion. The initial diameter d' is selected such that it corresponds with the desired initial diameter of the body vessel at the implantation position of the endoprosthesis device 10. After the desired expansion of the endoprosthesis device 10, the balloon catheter can be collapsed and removed in the conventional manner from the body.

In the unexpanded configuration, the sleeve member 12 is substantially annular in cross section. The initially expanded sleeve member 12 has a C-shaped configuration in cross section as best shown in FIG. 4. The open region 30 of the C-shape, or the region between the opposing edges 26,28, can be positioned to accommodate branch vessels as described above. In pediatric patients, the open region 30 is available for cellular growth of the endothelial layer of the body vessel thereby allowing for circumferential growth of the body vessel.

When necessary, to allow expansion to a second circumference of diameter d" to accommodate vessel growth or prevent restenosis, the connecting strips can be disjoined. In one embodiment the balloon catheter is reinserted and inflated at a pressure four to ten atmospheres causing the connecting strips to rupture or break allowing the sleeve member 12 to further expand, thereby enlarging the open region 30, or C-shape. This allows the sleeve member 12 to conform to the expanded circumference of the body vessel as for example in the pediatric patient. In an embodiment where the connecting strip 22 is formed from an absorbable suture material and the sleeve member 12 is formed in a self-expandable configuration, when the suture dissolves the sleeve member 12 can self-expand to conform to the expanded configuration.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. A method for fabricating a radially expandable endoprosthesis device comprising the steps of
    forming an elongated radially outwardly expandable sleeve member (12) including a wall (14) and a longitudinal axis (20) extending through the length thereof,
    forming at least one lateral slot (24) parallel to said longitudinal axis (20) disposed in said wall (14) including a pair of opposing edges (26,28) extending parallel of said longitudinal axis (20) and defining an open region (30) between the opposing edges (26,28),
    forming expansion limiting means including at least one connecting strip (22),
    disposing the expansion limiting means on the sleeve member (12) across the lateral slot (24) for initially limiting to a first circumference the radially outward expansion of the sleeve member (12).

2. The method of claim 1 wherein the step of forming the expansion limiting means includes fabricating the expansion limiting means from a material that ruptures above a predetermined pressure.

3. The method of claim 1 wherein the step of forming the expansion limiting means includes fabricating the limiting means from an absorbable suture material.

4. The method of claim 1 wherein the step of forming a lateral slot including a pair of opposing edges (26,28) includes depositing a radiopaque material along the opposing edges (26,28).

5. The method of claim 1 wherein the step of forming the expansion limiting means includes operatively connecting the opposing edges (26,28) with the connecting strip (22).

6. A method for reinforcing a vessel with an endoprosthesis device (10) while allowing for secondarily reinforcing the vessel following further radial change of the vessel comprising the steps of:
    positioning an elongated sleeve member (12), including a wall (14), a longitudinal axis (20) extending through a length thereof, at least one lateral slot (24) parallel to the longitudinal axis (20) in the wall (14), the sleeve member (12) being expandable radially outwardly relative to said longitudinal axis (20), in an unexpanded configuration transluminally within a body vessel;
    expanding the sleeve member (12) radially outwardly thereby expanding the lateral slot (24);
    limiting the radially outward expansion of the sleeve member (12) initially to a first circumference corresponding to the lumen of the body vessel by at least one connecting strip (22) disposed across the lateral slot (24); and
    removing the limiting of radially outward expansion thereby allowing further expansion of the lateral slot (24) and secondary expansion of the sleeve member (12) to accommodate further radial change of the vessel.

7. The method of claim 6 wherein the step of disposing the connecting strip (22) on the sleeve member includes girdling circumferentially the sleeve member (12) with the connecting strip (22).

8. The method of claim 6 wherein the step of removing the limiting of radially outward expansion includes disjoining the connecting strip (22).

9. The method of claim 8 wherein the step of disjoining the connecting strip (22) is accomplished by the connecting strip (22) being composed of a material that ruptures above a certain pressure.

10. The method of claim 6 wherein the step of positioning the sleeve member (12) transluminally includes positioning to accommodate branching vessels.

11. The method of claim 10 wherein the step of positioning the sleeve member (12) transluminally includes the step of accommodating branching vessels by positioning the lateral slot (24) in front of the branching vessel.

12. The method of claim 11 wherein the step of positioning the lateral slot (24) in front of the branching vessel is accomplished by imaging a radiopaque lining (32) of the opposing edges (26,28).

13. The method of claim 6 wherein the expanding steps comprise expanding the sleeve member (12) with a balloon catheter.

14. A method for reinforcing a vessel with an endoprosthesis device (10) while allowing for radial growth of the vessel comprising the steps of
    preparing an elongated sleeve member (12), including a longitudinal axis (20) extending through a length thereof, the sleeve member (12) being expandable radially outwardly relative to said longitudinal axis (20), forming at least one open lateral slot (24) parallel to the longitudinal axis (20) in the sleeve member (12), and forming a pair of opposing edges within the lateral slot (24) parallel to the longitudinal axis (20) with expansion limiting means including at least one connecting strip (22) disposed across the lateral slot (24), positioning the elongated sleeve member (12), in an unexpanded configuration transluminally within a lumen of a body vessel, expanding the sleeve member (12) radially outwardly to a first circumference corresponding to the lumen of the body vessel and maintaining the expansion by the expansion limiting means thereby opening up the lateral slot (24) between the opposing edges (26,28) forming an open region (30) for growth of the vessel; and expanding the sleeve member (12) radially outwardly by continuing to open up the lateral slot (24), as the vessel grows circumferentially, by disengaging the expansion limiting means.

* * * * *